(12) United States Patent
Castagna et al.

(10) Patent No.: US 8,753,869 B2
(45) Date of Patent: Jun. 17, 2014

(54) CARTRIDGE FOR BIOCHEMICAL ANALYSES, SYSTEM FOR BIOCHEMICAL ANALYSES, AND METHOD OF CARRYING OUT A BIOCHEMICAL PROCESS

(75) Inventors: Maria Eloisa Castagna, Catania (IT); Giuseppe Catania, Messina (IT); Salvatore Leonardi, Aci S. Antonio (IT); Alberto Mario Piro, Acireale (IT)

(73) Assignee: STMicroelectronics S.R.L., Agrate Brianza (IT)

( * ) Notice: Subject to any disclaimer, the term of this patent is extended or adjusted under 35 U.S.C. 154(b) by 0 days.

(21) Appl. No.: 13/531,303

(22) Filed: Jun. 22, 2012

(65) Prior Publication Data
US 2013/0004952 A1 Jan. 3, 2013

(30) Foreign Application Priority Data

Jun. 28, 2011 (IT) .............................. TO2011A0567

(51) Int. Cl.
*C12M 1/00* (2006.01)
*C12Q 1/68* (2006.01)
*C12M 1/34* (2006.01)
*G01N 21/00* (2006.01)
*A61J 1/06* (2006.01)
*G01J 3/30* (2006.01)
*G01N 21/25* (2006.01)

(52) U.S. Cl.
USPC ... 435/283.1; 435/6.1; 435/287.2; 422/82.05; 422/554; 356/317; 356/417

(58) Field of Classification Search
USPC ............. 435/6.1, 283.1, 287.2; 356/317, 417, 356/435, 456, 458; 422/82.05, 554
See application file for complete search history.

(56) References Cited

U.S. PATENT DOCUMENTS

| 6,325,977 | B1 * | 12/2001 | Theil ......................... 422/82.05 |
| 2002/0045272 | A1 * | 4/2002 | McDevitt et al. ............. 436/518 |
| 2009/0013768 | A1 * | 1/2009 | Pouteau et al. .............. 73/61.48 |
| 2009/0325164 | A1 * | 12/2009 | Vossenaar et al. ................ 435/6 |
| 2011/0312841 | A1 * | 12/2011 | Silverbrook et al. ........... 506/40 |

FOREIGN PATENT DOCUMENTS

| EP | 1964610 A2 | 9/2008 |
| WO | 2004/017374 A2 | 2/2004 |
| WO | 2008/055680 A1 | 5/2008 |

OTHER PUBLICATIONS

Iordanov et al, PCR Array on Chip—Thermal Characterization, 2003, Sensors, Proceedings of IEEE, 2, 1045-1048.*
Search Report and Written Opinion, dated Feb. 8, 2012, from IT TO20110567.

* cited by examiner

*Primary Examiner* — Narayan Bhat
(74) *Attorney, Agent, or Firm* — McDonnell Boehnen Hulbert & Berghoff LLP

(57) ABSTRACT

A cartridge for biochemical analysis includes a support, a structure, which is set on the support and contains wells for receiving a solution, and photodetectors on the support, in positions corresponding to respective wells.

14 Claims, 6 Drawing Sheets

CARTRIDGE FOR BIOCHEMICAL ANALYSES, SYSTEM FOR BIOCHEMICAL ANALYSES, AND METHOD OF CARRYING OUT A BIOCHEMICAL PROCESS

BACKGROUND

The present disclosure relates to a cartridge for biochemical analyses, a system for biochemical analyses, and a method of carrying out a biochemical process.

As is known, analysis of nucleic acids involves, according to different modalities, preliminary steps of preparation of a specimen of biological material, amplification of the nucleic material contained therein, and hybridization of individual target or reference strands, corresponding to the sequences sought. Hybridization occurs (and the test yields a positive result) if the specimen contains strands complementary to the target strands.

At the end of the preparatory steps, the specimen is examined to check whether hybridization has taken place (the so-called "detection step").

Several inspection methods and apparatuses are known for this purpose, for example of an optical or electrical type. In particular, the methods and apparatuses of an optical type are frequently based upon the phenomenon of fluorescence. The amplification and hybridization reactions are conducted in such a way that the hybridized strands, contained in a detection chamber provided in a support, include fluorescent molecules or fluorophores (the hybridized strands can be fixed to the bottom of the detection chamber or else remain in liquid suspension). The support is exposed to a light source having an appropriate spectrum of emission such as to excite the fluorophores. In turn, the excited fluorophores emit a secondary radiation at a wavelength of emission higher than that of the peak of the excitation spectrum. The light emitted by the fluorophores is collected and detected by means of an optical sensor. In order to eliminate the background light radiation, which represents a source of disturbance, the optical sensor is provided with bandpass filters centred at the wavelength of emission of the fluorophores.

The detection of different substances in one and the same specimen usually involves the use of distinct fluorophores, which have respective excitation and emission wavelengths. Light sources with different spectra of emission are hence used in succession to analyse the responses in the excitation and emission bands of each fluorophore.

A limitation of the known systems lies in the difficulty of illuminating in a uniform way the portion of the support in which the material to be analysed is contained. Frequently, in fact, the supports comprise plates in which wells are made orderly arranged to form a matrix array. The supports are loaded in lightproof chambers of analyser apparatuses for being read. On account of constructional constraints of the sources and of the analyser apparatuses, the area of the light source, for example a LED, its directionality and its distance from the support, the entire array is not illuminated uniformly, resulting in variations of incident optical power from one well to the other. Since the fluorophores are excited by the incident optical power, their response can be affected by the non-uniform illumination.

On the other hand, using a number of light sources with one and the same nominal spectrum of emission would not prevent variations of illumination due to process dispersions.

It should moreover be considered that the optical power supplied by the light source is not constant over time, but varies for example in proportion to the ambient temperature and can undergo modifications due to ageing of the component.

Hence, the non-uniform and non-constant illumination can lead to unreliable readings.

SUMMARY

In one aspect, certain embodiments described herein relate to a cartridge for biochemical analyses. The cartridge comprises: a support; a transparent layer on the support, wherein the transparent layer is transparent to light radiation in substantially the entire visible spectrum; a structure on the transparent layer, the structure defining a plurality of wells for receiving a material to be analyzed; and a plurality of photodetectors on the support in positions corresponding to respective wells in the structure.

In another aspect, certain embodiments described herein relate to a system for biochemical analyses. The system comprises an analyzer and a control unit. The analyzer comprises a light source configured to illuminate a plurality of positions with light radiation. The analyzer is configured to receive a plurality of wells such that each position is occupied by a respective well. The analyzer is also configured to receive a plurality of photodetectors such that each position is occupied by a respective photodetector. The analyzer further comprises an image sensor configured to acquire images of the plurality of wells occupying the plurality of positions and illuminated with the light radiation from the light source. The control unit is configured to determine for each position an incident optical power of the light radiation from the light source based on an output of a photodetector occupying that position and to compensate the images of the illuminated wells as a function of the incident optical power determined for the positions.

In some of these embodiments, the plurality of wells and the plurality of photodetectors are located in a cartridge such that each well has a corresponding photodetector. The analyzer is configured to receive the cartridge such that each position is occupied by a respective well and a respective photodetector.

In other of these embodiments, the plurality of wells is located in a microreactor cartridge and the plurality of photodetectors is located in a calibration cartridge separate from the microreactor cartridge. The analyzer is configured to receive the microreactor cartridge such that each position is occupied by a respective well. The analyzer is configured to receive the calibration cartridge such that each position is occupied by a respective photodetector.

In yet another aspect, certain embodiments described herein relate to a method. A plurality of photodetectors is illuminated with excitation radiation from a light source, wherein the photodetectors are located at a plurality of positions relative to the light source. For each position, an incident optical power of the excitation radiation from the light source is determined based on an output of the photodetector at that position. A plurality of wells is illuminated with excitation radiation from the light source. The wells contain fluorophore and are located at the plurality of positions relative to the light source. An image is acquired using an image sensor. The image corresponds to fluorescence radiation that is emitted by the fluorophore contained in the wells in response to the excitation radiation from the light source. A portion of the image corresponding to a particular well is compensated based on the incident power determined for the position of that particular well.

In some of these embodiments, the plurality of wells and the plurality of photodetectors are located in a cartridge such that each well has a corresponding photodetector. In other of these embodiments, the plurality of wells is located in a microreactor cartridge and the plurality of photodetectors is located in a calibration cartridge separate from the microreactor cartridge.

BRIEF DESCRIPTION OF THE DRAWINGS

Non-limiting examples will now be described with reference to the attached drawings, wherein.

DETAILED DESCRIPTION

Figure 1:
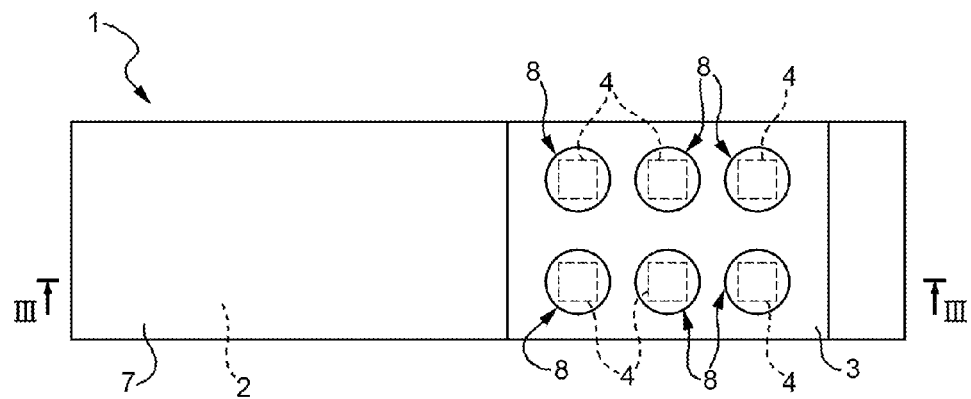
FIG. 1 is a top plan view of a cartridge for biochemical analyses according to one embodiment.
Figure 2:
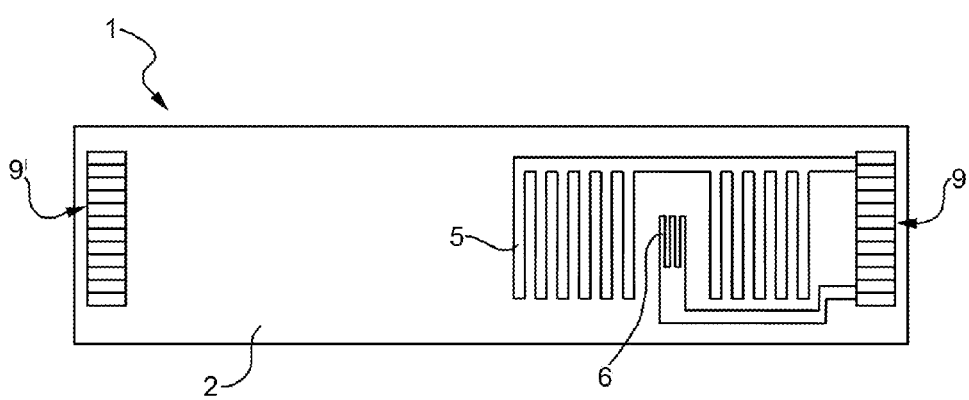
FIG. 2 is a plan view from beneath of the cartridge of FIG. 1.
Figure 3:
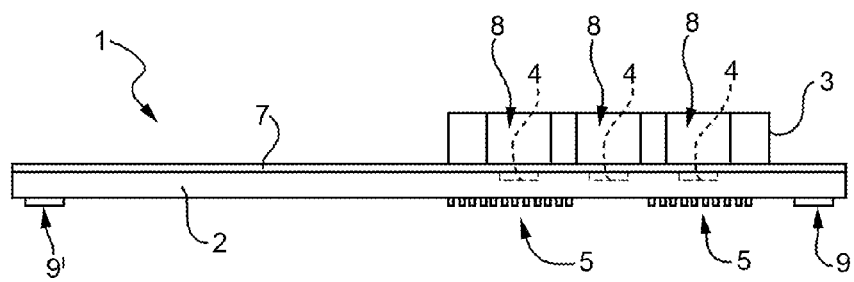
FIG. 3 is a side view of the cartridge of FIG. 1, sectioned in the plane of trace III-III of FIG. 1.

FIGS. 1-3 show a disposable cartridge for biochemical analyses, designated as a whole by the reference number 1. The cartridge 1 comprises a support 2, a well module 3, photodetectors 4, a heater 5, and a temperature sensor 6, which together form a microreactor.

For reasons of simplicity, hereinafter reference will be made to cartridges and instrumentation for the amplification of nucleic acids by means of PCR (Polymerase Chain Reaction) and the analysis of the results of the amplification, without on the other hand this possibly being considered as in any way limiting the scope of the invention. What is described hereinafter, in fact, finds advantageous application also in systems for execution and detection of the results of different biochemical processes, in addition to amplification by PCR.

In one embodiment, the support 2 is a chip made of semiconductor material, for example monocrystalline silicon, and has a rectangular shape. Furthermore, a face 2a of the support 2 is coated with a biocompatible passivation layer 7. Layer 7 could be transparent to light radiation in substantially the entire visible spectrum. For example, layer 7 could be silicon oxide.

The well module 3 is made of preferably transparent polymeric material and is fixed on the passivation layer 7 of the support 2, for example by gluing. The well module 3 has a plurality of through cavities, which, with the underlying passivation layer 7, define wells 8 for receiving a specimen of biological material to be analysed. In one embodiment, the wells 8 are six in number and are arranged to form a matrix.

In one embodiment, moreover, the cartridge 1 has been functionalized by fixing DNA probes to the walls of the wells 8. The DNA probes can comprise individual DNA strands containing target sequences of nucleotides to be sought in the biological specimen analysed.

The photodetectors 4, for example phototransistors or photodiodes, are integrated in the support 2, flush with the face 2a, and are obtained through conventional semiconductor manufacturing techniques. In greater detail, the photodetectors 4 are arranged in positions corresponding to respective wells 8, immediately underneath the passivation layer 7. In this way, the light radiation that impinges upon the cartridge 1 on the side of the face 2a of the support 2 reaches the photodetectors 4 through the well module 3 and the passivation layer 7.

The photodetectors 4 are connected, by through vias and electrical-connection lines (not illustrated for reasons simplicity), to contact pads 9a set at a longitudinal end of the support 2 to form a connector 9. In the embodiment of FIGS. 1 to 3, a connector 9' replicates the connector 9 at an opposite longitudinal end of the support 2.

The heater 5 and the temperature sensor 6 are provided on one face 2b of the support 2, opposite to the face 2a, in positions corresponding to the wells 8. The heater 5 and the temperature sensor 6 are thermally coupled to the well module 3 in such a way that the thermal energy released by the heater 5 causes heating of the biological material in the wells 8, and the temperature measurements supplied by the temperature sensor 7 are indicative of the temperature in the wells 8. The heater 5 is defined by a conductive path, for example made of metal or polysilicon. The temperature sensor 6 is of a thermoresistive type. In practice, the resistance varies as a function of the temperature, and hence a reading of the resistance is indicative of the temperature at a given instant.

In order to carry out analyses of a specimen with the cartridge 1, a mixture of reagents in solution, which comprises fluorophores of two types, is introduced into the wells 8. A first type of fluorophores has an excitation wavelength $\lambda_{E1}$ and a detection (or emission) wavelength $\lambda_{D1}$ and combines with a first substance to be sought. A second type of fluorophores has an excitation wavelength $\lambda_{E2}$ and a detection (or emission) wavelength $\lambda_{D2}$, and combines with a second substance to be sought.

Figure 4:
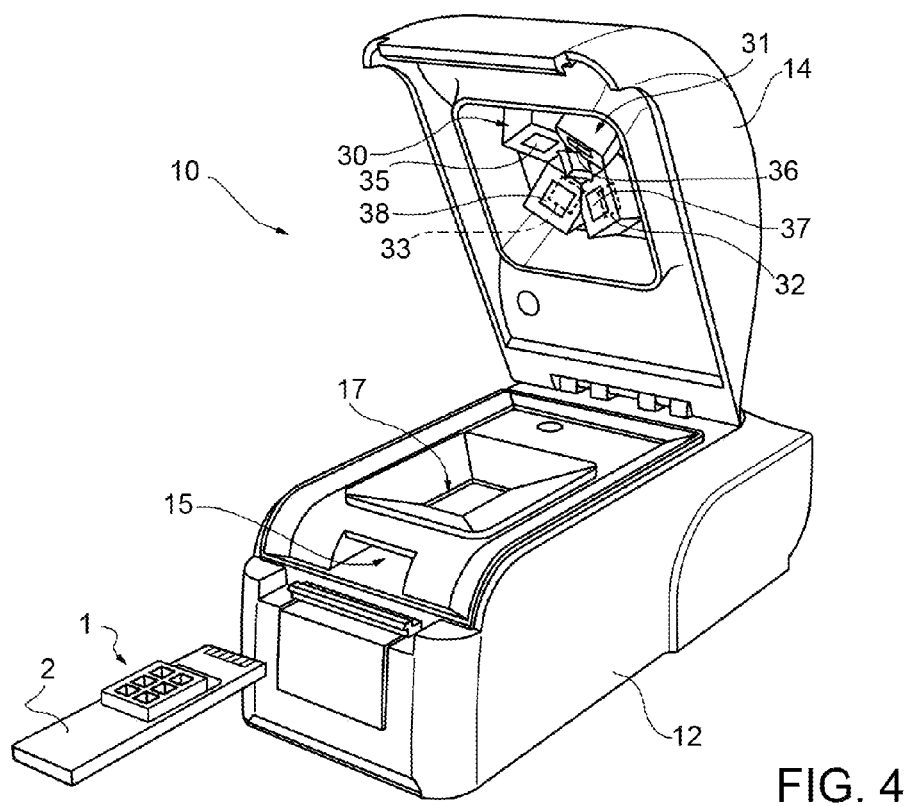
FIG. 4 is a perspective view of an analyser for biochemical analyses.

As illustrated in FIG. 4, a real-time PCR analyser, designated as a whole by the reference number 10, comprises a first shell 12, closed at the bottom by a metal plate 13, and a second shell 14, hinged to the first shell 12. The first shell 12, the metal plate 13, and the second shell 14 define a casing of the analyser 10.

Figure 5:
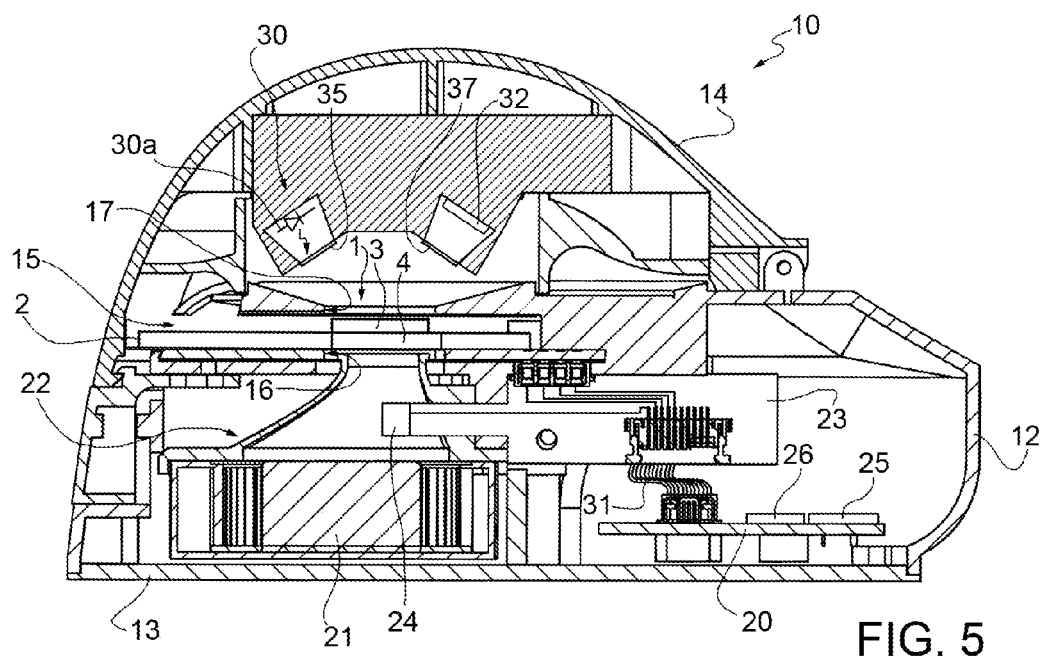
FIG. 5 is a side view, sectioned in a longitudinal plane, of the analyser of FIG. 4.

With reference also to FIG. 5, the first shell 12 has a slot 15 for receiving the cartridge 1. The slot 15 is accessible from outside for insertion of the cartridge 1 when the second shell 12 is open in the raised position. In the position corresponding to the position of the well module 3 inserted in the slot 15, the first shell 12 has a first window 16 and a second window 17. The first window 16 sets the slot 15 in communication with the inside of the first shell 12, whilst the second window 17 enables observation of the well module 3 when the cartridge 1 is inserted in the slot 15 and the second shell 14 is raised.

A control card 20, a fan 21, a manifold 22, and a sensor card 23, mounted on which is a calibrated temperature sensor 24, are housed within the first shell 12 (FIG. 5).

The control card 20 and the fan 21 are fixed to the metal plate 13.

The control card 20 houses a control unit 25, which presides over operation of the analyser 10, as explained hereinafter, and at least one memory module 26.

In the embodiment described herein, the fan 21 is aligned to the windows 16, 17 and may be actuated so as to suck in air through the manifold 22. More precisely, a flow of air is taken in along a path that develops from the slot 15 to the fan 21 through the manifold 22 so as to cause heat exchange between the flow of air and the cartridge 1 loaded in the slot 15.

The second shell 14 is hinged to the first shell 12 and defines a lid, shaped so as to light-proof mate with the first shell 12 and obscure the second window 17. In practice, when the second shell 14 is closed on the first shell 12, the inside of the second shell 14 is substantially inaccessible to the light, and the cartridge 1 inserted in the slot 15 (in particular the well module 3) is obscured. When the second shell 14 is raised, the slot 15 is accessible for inserting and removing the cartridge 1. In addition, when the cartridge 1 is located in the slot 15, the well module 3 is visible and accessible from outside to enable operations of loading of biological specimens to be analysed.

Figure 6:
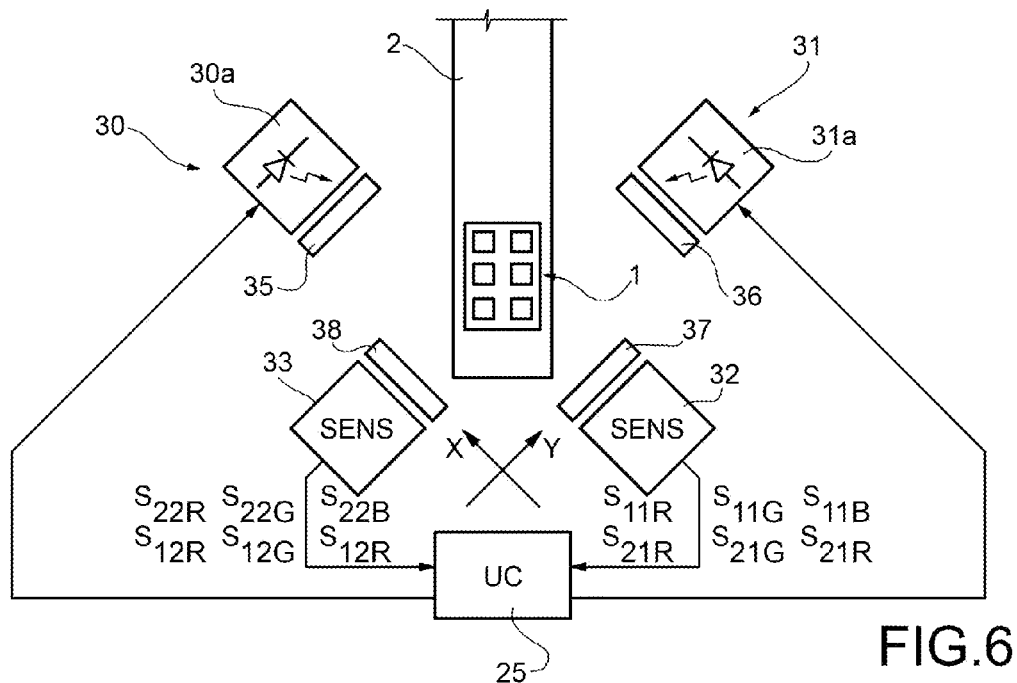
FIG. 6 is a top plan view of a detail of the analyser of FIG. 2, with parts removed for reasons of clarity.

Housed in the second shell 14 are a first light source 30, a second light source 31, a first image sensor 32, and a second image sensor 33, all controlled by the control unit 25, as illustrated also in FIG. 6.

Figure 7:
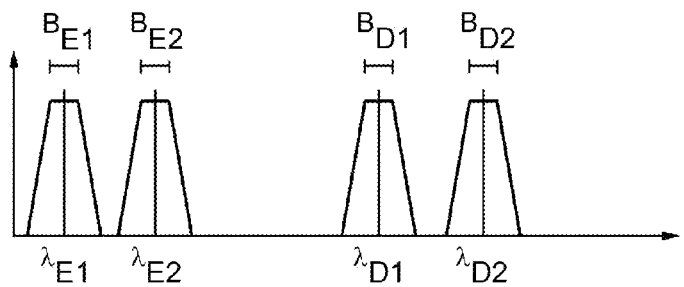
FIG. 7 is a graph that shows quantities corresponding to the analyser of FIG. 2.

The first light source 30 and the second light source 31, which comprise respective emitter devices 30a, 31a, for example of the LED type, are oriented so as to illuminate the cartridge 1 through the second window 17 and are provided, respectively, with a first excitation filter 35 and a second excitation filter 36, which intercept the radiation coming from the emitter device 30a and from the emitter device 31a, respectively. As illustrated in FIG. 7, the first excitation filter 35 and the second excitation filter 36 have respective excitation passbands $B_{E1}$, $B_{E2}$ centred around excitation wavelengths $\lambda_{E1}$, $\lambda_{E2}$ of fluorophores of two different types. The light radiation supplied by the first light source 30 and by the second light source 31 is hence substantially confined, respectively, in the excitation passband $B_{E1}$ and in the excitation passband $B_{E2}$ of the first excitation filter 35 and of the second excitation filter 36. The excitation passbands $B_{E1}$, $B_{E2}$ are moreover separate and non-overlapping.

The first image sensor 32 and the second image sensor 33 are arranged so as to receive the light emitted by the fluorophores present in the specimen contained in the cartridge 1 and excited by the light coming from the first light source 30 and from the second light source 31. In the embodiment described, the first light source 30 and the first image sensor 32 are aligned along a first axis X, parallel to the plane of the support 2 when the latter is located in the slot 15 and rotated through 45° with respect to a longitudinal axis of the support 2 in the slot 15. The second light source 31 and the second image sensor 33 are aligned along a second axis Y, perpendicular to the first axis X (FIG. 6).

The first image sensor 32 and the second image sensor 33 are provided, respectively, with a first detection filter 37 and a second detection filter 38. The first detection filter 37 and the second detection filter 38 have respective detection passbands $B_{D1}$, $B_{D2}$ centred around detection (emission) wavelengths $\lambda_{D1}$, $\lambda_{D2}$ of fluorophores of two different types (FIG. 7). The passbands $B_{D1}$, $B_{D2}$ of the first detection filter 37 and of the second detection filter 38 are moreover separate and non-overlapping, and exclude, respectively, the passbands $B_{E1}$, $B_{E2}$ of the first excitation filter 35 and of the second excitation filter 36.

In the embodiment described, moreover, the first image sensor 32 and the second image sensor 33 are RGB sensors, each of which supplies three respective signals for the red, green, and blue channels. In fact, the RGB sensors comprise a plurality of photodetectors arranged in a matrix and each provided with a respective red, green, or blue filter, with the green elements in a proportion that is twice that of the red and blue elements. One RGB sensor hence supplies three channel signals, one for each of the fundamental colours red, green, and blue, which are then combined with local-mean operators for reconstructing the original colours of the image acquired. Each image signal hence represents the same image filtered with a filter corresponding to one of the fundamental colours.

In particular, the first image sensor 32 supplies first channel signals, and the second image sensor 33 supplies second channel signals. More precisely, the first image sensor 32 supplies first channel signals $S_{11R}$, $S_{11G}$, $S_{11B}$, when the first light source 30 is activated, and first channel signals $S_{12R}$, $S_{12G}$, $S_{12H}$ when the second light source 31 is activated, and the second image sensor 33 supplies second channel signals $S_{21R}$, $S_{21G}$, $S_{21H}$ when the first light source 30 is activated, and second channel signals $S_{22R}$, $S_{22G}$, $S_{22B}$ when the second light source 31 is activated. In what follows, the expression "image signals $S_I$" is used to designate all the channel signals $S_{11R}$, $S_{11G}$, $S_{11B}$, $S_{12R}$, $S_{12G}$, $S_{12B}$, $S_{21R}$, $S_{21G}$, $S_{21B}$, $S_{22R}$, $S_{22G}$, $S_{22B}$ for one and the same image or portion of image (possibly even just a single pixel).

The signals supplied by the first image sensor 32 and by the second image sensor 33 hence contain information regarding the response of each type of fluorophore in the bands of the fundamental colours when either one or the other between the first light source 30 and the second light source 31 is activated.

The control unit 25 exploits the image signals $S_I$ and information preliminarily stored in the memory module 26 to determine the presence and the concentrations (possibly zero) in the specimen of substances under examination, to which the fluorophores have bound.

Figure 8:
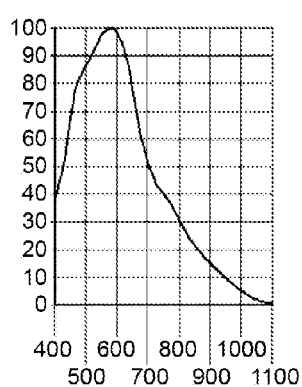
FIGS. 8 and 9 show graphs corresponding to components of the cartridge of FIG. 1.
Figure 9:
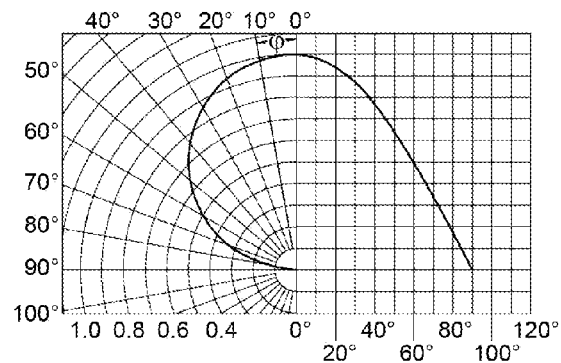

For each photodetector 4, the memory module 26 contains:
a response curve C1 (FIG. 8) calibrated and normalized as a function of the wavelength of the incident radiation (at least one respective response value for the central wavelength of each of the light sources 30, 31 present);
a response curve C2 (FIG. 9) calibrated and normalized as a function of the angle of incidence;
an angle of incidence of the incident radiation for each of the light sources 30, 31 present; and
a relative position with respect to each of the light sources 30, 31 present.

The control unit 25 presides over operation of the analyser 10 and controls the execution principally of a thermal cycle to obtain amplification of the nucleic acids present in the biological material, for example by the PCR ("Polymerase Chain Reaction") technique, of a procedure of optical detection of specific nucleotide sequences ("target DNA").

The cartridge 1 is inserted in the slot 15, and a solution containing a specimen of biological material and the ingredients for the amplification process is introduced into the wells 8. Among the other ingredients, the solution comprises nucleotides (G, A, T, C), primers, a DNA-polymerase enzyme (for example, TAQ-polymerase), fluorophores, and DNA probes containing single target strands. The control unit 25 drives the heater 5 and the fan 21, respectively, to supply and subtract thermal energy in such a way that the temperature in the wells 8 varies cyclically according to a pre-determined profile, which enables the amplification reactions (in brief, denaturation, annealing, extension and hybridization for the PCR). If the specimen to be analysed contains sequences complementary to the DNA probes, during the step of hybridization fluorophores are incorporated in the hybridized strands, which are rendered optically detectable. The correspondence of the temperature to the desired profile is verified using the temperature sensor 6.

Figure 10:
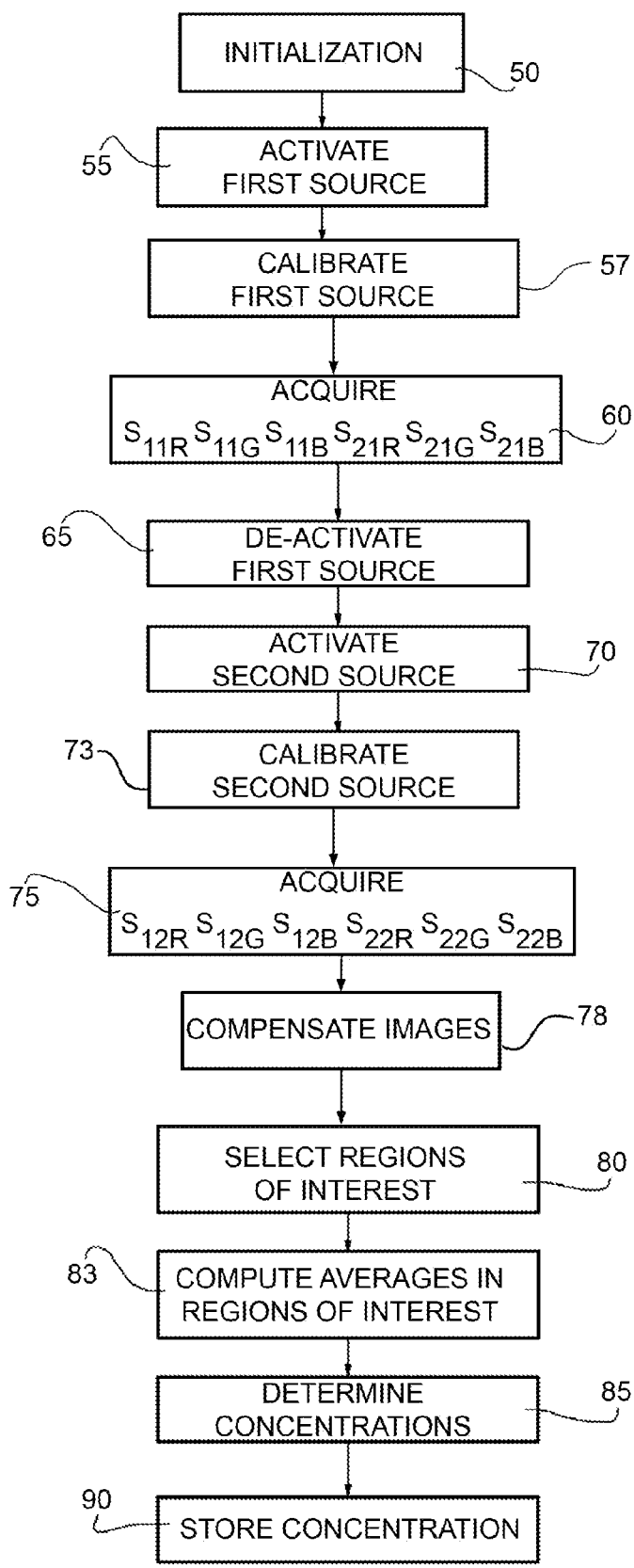
FIG. 10 is a flowchart regarding a method of carrying out a biochemical process according to one embodiment.

For the detection of hybridized strands, which contain fluorophores, the control unit 25 uses the procedure described hereinafter with reference to FIG. 10.

After an initialization step (block 50), the control unit 25 activates the first light source 30 (block 55) and carries out a calibration (block 57). In this step, the control unit 25 uses the photodetectors 4 in order to determine the optical power incident on the various wells 8 as a result of the emission by the first light source 30. The control unit 25 fetches from the memory module 26 normalized response values of the photodetectors 4 for the wavelength and the angle of incidence for the first light source 30. Then, the output of the photodetectors 4 is read and processed to obtain the effective incident optical power, for example through the following relation:

$$PI_{I1} = SD_{I1}/(R_\lambda(\lambda_{E1})R_\phi(\phi_1))$$

where: $PI_{I1}$ is the optical power incident on the i-th photodetector 4 when the first light source 30 is activated; $R_\lambda(\lambda_{E1})$ and $R_\phi(\phi_1)$ are the responses of the i-th photodetector 4, respectively, as a function of the wavelength $\lambda_{E1}$ and as a function of the angle of incidence $\phi_{1I}$ of the radiation supplied by the first light source 30 through the first excitation filter 35; and $SD_{I1}$ is the output of the i-th photodetector 4.

The values of incident optical power detected are stored in the memory module 26.

Once the step of calibration of the first light source 30 is through, the control unit 25 acquires (block 60) both the first channel signals $S_{11R}$, $S_{11G}$, $S_{11B}$, associated to the fluorophores of the first type with detection wavelength $\lambda_{D1}$ (which respond to the excitation wavelength $\lambda_{E1}$ of the first light source 30), and the second channel signals $S_{21R}$, $S_{21G}$, $S_{21B}$, associated to the fluorophores of the second type with detection wavelength $\lambda_{D2}$ (which respond principally to the excitation wavelength $\lambda_{E2}$ of the second light source 31 and, secondarily, to tails of the excitation passband $B_{E1}$ of the first light source 30).

Next, the control unit 25 deactivates the first light source (block 65), activates the second light source 31 (block 70), and carries out a new calibration (block 73). The control unit 25 uses the photodetectors 4 to determine the optical power incident on the various wells 8 as a result of the emission of the second light source 31. The control unit 25 fetches from the memory module 26 normalized response values of the photodetectors 4 for the wavelength and the angle of incidence corresponding to the second light source 31. Then, the output of the photodetectors 4 is read and processed to obtain the effective incident optical power, for example through the following relation:

$$PI_{I2} = SD_{I2}/(R_\lambda(\lambda_{E2})R_\phi(\phi_2)),$$

where: $PI_{I2}$ is the optical power incident on the i-th photodetector 4 when the second light source 31 is activated; $R_\lambda(\lambda_{E2})$ and $R_\phi(\phi_2)$ are the responses of the i-th photodetector 4 respectively as a function of the wavelength $\lambda_{E2}$ and as a function of the angle of incidence $\phi_{2I}$ of the radiation supplied by the second light source 31 through the second excitation filter 36; and $SD_{I1}$ is the output of the i-th photodetector 4.

The values of incident optical power detected are stored in the memory module 26.

Then, the control unit 25 acquires (block 75) both the first channel signals $S_{12R}$, $S_{12G}$, $S_{12B}$ associated with the fluorophores of the first type with detection wavelength $\lambda_{D1}$ (which respond to the excitation wavelength $\lambda_{E1}$ of the first light source 30 and, secondarily, to tails the excitation passband $B_{E2}$ of the second light source 31), and the second channel signals $S_{22R}$, $S_{22G}$, $S_{22B}$, associated with the fluorophores of the second type with detection wavelength $\lambda_{D2}$ (which respond principally to the excitation wavelength $\lambda_{E2}$ of the second light source 31).

The image signals $S_I$ thus obtained represent images defined by a matrix of points (pixels), which are corrected by the control unit 25 so as to take into account the conditions of non-uniform illumination and hence the different response of the fluorophores (block 78). In particular, the luminosity of the pixels is compensated on the basis of the values of incident power detected at the wells 8 by the photodetectors 4 during the steps of calibration of each light source 30, 31.

The luminosity for each single pixel in the configuration used is in fact proportional to the power of fluorescence detected by the image sensors through the respective of detection filters. In fact, the power of fluorescence is linked to the excitation power (incident optical power) by the following relation:

$$P_{FLU} = P_I \cdot C_{MOL} \cdot QY \cdot \epsilon \cdot d$$

where $P_{FLU}$ is the power of fluorescence, PI is the optical power incident on the biological material, $C_{MOL}$ is the concentration molar, QY is the quantum yield (characteristic of the fluorophore), $\epsilon$ is the coefficient of molar extinction (characteristic of the fluorophore), and d is the thickness of material traversed.

Since the fluorescence power $P_{FLU}$ depends upon the incident power $P_I$, the signal acquired by the image sensors in the portions of image for the regions of interest is compensated as a function of the values of incident power acquired by the photodetectors 4.

For example, applied to the luminosity of the pixels is a coefficient of normalization at the maximum value of incident power detected by the photodetectors 4 in the regions of interest. The normalization coefficient for the pixels of a portion of image (in particular, corresponding to one of the wells 8) can be calculated on the basis of the ratio between the maximum value of incident power detected by the photodetectors 4 and the value of incident power determined for the individual i-th well by the corresponding photodetector 4.

Next (block 80), the control unit 25 selects in the image regions of interest, eliminating the portions of image devoid of significant information. In the embodiment described, in particular, the regions of interest selected correspond to the wells 8 of the cartridge 1.

Then (block 83), the image signals $S_I$ acquired are averaged over each region of interest, which is hence represented by a respective measurement vector $$S = [S_{11R}*S_{11G}*S_{11B}*S^{12R}*S_{12G}*S_{12B}*S_{21R}*S_{21G}*S_{21B}*S_{22R}*S_{22G}*S_{22B}*]$$

(where the prime symbol indicates the transpose; the measurement vector S is consequently a column vector). The symbol "*" indicates the respective mean value of each image signal $S_I$ in the region of interest.

The control unit 25 then processes the image signals $S_I$ detected for determining the concentrations $C_1$, $C_2$ of the fluorophores and hence of the substances sought in the specimen being examined (block 85).

For this purpose, it may be noted that the relation $$S = MC \qquad (1)$$

applies, where $C=[C_1\ C_2]'$ is the column vector of the concentrations sought, and M is a cross-talk matrix defined as follows:

$$M = \begin{bmatrix} f_{111R} & f_{211R} \\ f_{111G} & f_{211G} \\ f_{111B} & f_{211B} \\ f_{112R} & f_{212R} \\ f_{112G} & f_{212G} \\ f_{112B} & f_{212B} \\ f_{121R} & f_{221R} \\ f_{121G} & f_{221G} \\ f_{121B} & f_{221B} \\ f_{122R} & f_{222R} \\ f_{122G} & f_{222G} \\ f_{122B} & f_{222B} \end{bmatrix}$$

In the first column of the cross-talk matrix M, the coefficients $f_{1JKR}$, $f_{1JKG}$, $f_{1JKB}$, represent the contributions, due to the first fluorophore, to the red, green and blue channels (signals $S_{JKR}$, $S_{JKG}$, $S_{JKB}$) detected by the sensor J (J=1, 2, corresponding, respectively, to the first image sensor 32 and to the second image sensor 33) when the light source K is active (K=1, 2, corresponding, respectively, to the first light source 30 and to the second light source 31). As in the second column of the cross-talk matrix M, the coefficients $f_{2JKR}$, $f_{2JKG}$, $f_{2JKB}$, represent the contributions due to the second fluorophore, to the red, green, and blue channels detected by the sensor J when the light source K is active.

The coefficients of the cross-talk matrix M can be determined experimentally by making measurements with standard calibration concentrations, or else analytically through a model or simulation, starting from the characteristic curves of the light sources, filters, image sensors, and fluorophores.

To determine the concentration vector C, the control unit 25 uses the pseudo-inverse cross-talk matrix $M_{PI}$, i.e., the matrix that satisfies the relation $$M_{PI}M=I_{(2\times 2)} \quad (2)$$

where $I_{(2\times 2)}$ is the identity matrix with two rows and two columns.

The concentration vector C is determined by the control unit 25 as follows:

$$C=M_{PI}S \quad (3)$$

The concentrations thus determined (block 90) are stored in the memory module 26 and made available by the control unit 25 through an interface (not illustrated), for example a USB interface.

The calibration made thanks to the photodetectors 4 enables effective compensation of the non-uniform illumination, preventing imprecision in the reading due to the fact that the incident optical power that excites the fluorophores is higher in some areas of the cartridge 1 and lower in others. The advantage is particularly important for portable analysers, which, in order to be easily transportable and used even outside the laboratory, must favour the reduction of the dimensions and of the weights at the expense of other constructional aspects. In particular, on account of the constraints imposed by the purposes of use it is difficult to adopt solutions that enable a good uniformity of illumination to be achieved.

In a different embodiment (illustrated in FIGS. 11-13), a cartridge 100 for biochemical analyses comprises a support 102, a well module 103, photodetectors 104, and a heater 105, which form a microreactor.

Also in this case, the support 102 is a chip of semiconductor material, for example monocrystalline silicon, and has a rectangular shape. Furthermore, a face 102a of the support 102 is coated with a biocompatible passivation layer 107. Layer 107 could be transparent to light radiation in substantially the entire visible spectrum. For example, layer 107 could be silicon oxide.

The well module 103 is made of preferably transparent polymeric material and is fixed on the passivation layer 107 of the support 102. The well module 103 has a plurality of through cavities that, with the underlying passivation layer 107, define as many wells 108 for receiving a specimen of biological material to be analysed.

The photodetectors 104, for example phototransistors or photodiodes, are integrated in the support 102 flush with the face 102a and are obtained by conventional semiconductor-manufacturing techniques. In greater detail, the photodetectors 104 are arranged in positions corresponding to respective wells 108, immediately underneath the passivation layer 107. In this way, the light radiation that impinges upon the cartridge 101 on the side of the face 102a of the support 102 reaches the photodetectors 104 through the well module 103 and the passivation layer 107.

Figure 11:
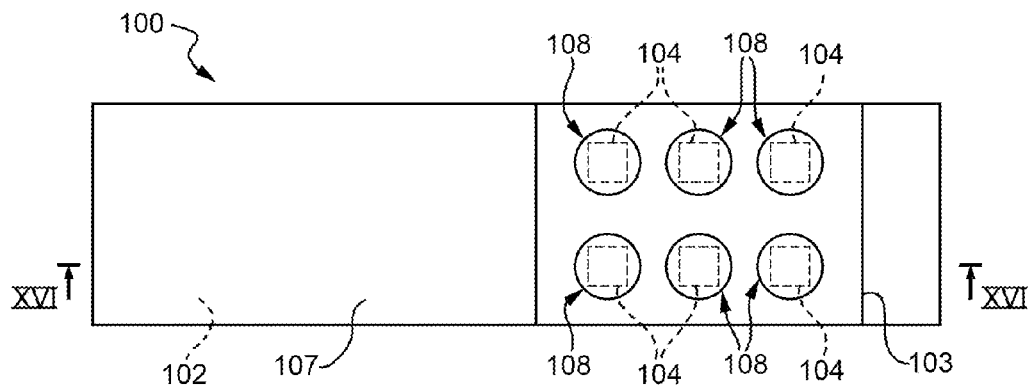
FIG. 11 is a top plan view of a cartridge for biochemical analyses according to a different embodiment.
Figure 12:
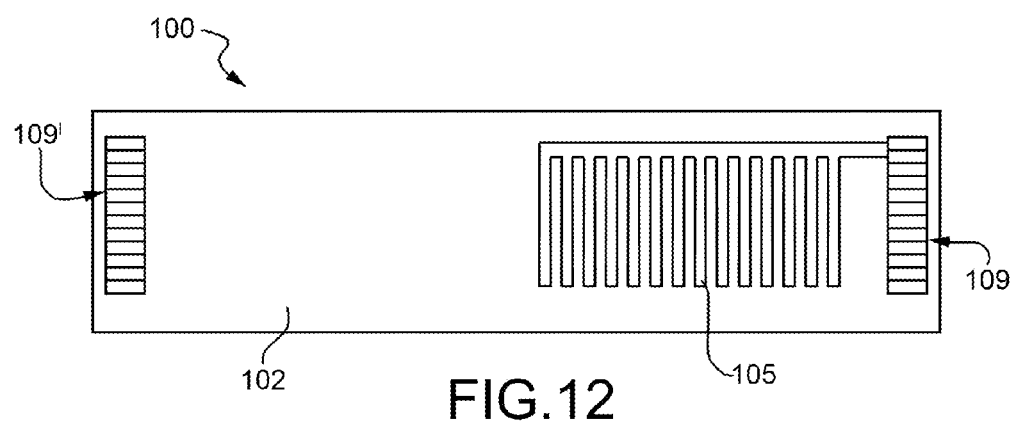
FIG. 12 is a plan view from beneath of the cartridge of FIG. 11.
Figure 13:
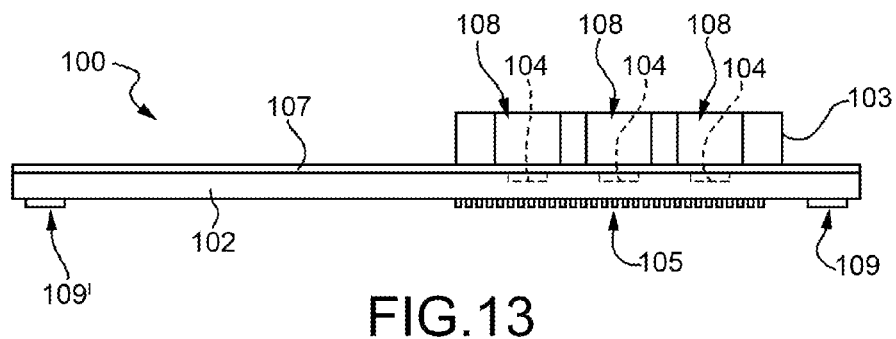
FIG. 13 is a side view of the cartridge of FIG. 11, sectioned in the plane of trace XIII-XIII of FIG. 11.

By through vias and electrical-connection lines (which for reasons simplicity are not illustrated), the photodetectors 104 are connected to contact pads 109a set at a longitudinal end of the support 102 to form a connector 109. In the embodiment of FIGS. 11-13, a connector 109' replicates the connector 109 at an opposite longitudinal end of the support 102.

The heater 105 is made on a face 102b of the support 102, opposite to the face 102a, and extends in a uniform way substantially over all the area corresponding to the well module 103. The heater 105 is thermally coupled to the well module 103 in such a way that the thermal energy released during operation causes heating of the biological material in the wells 108.

The cartridge 100 is inserted into the analyser 10. In this case, the control unit 25 is configured to use the photodetectors 104 as temperature sensors during the amplification step, which envisages the thermal cycle. Once the conditions of polarisation have been fixed, in fact, the voltage-current characteristic of the photodetectors 104 depends substantially only upon the temperature in the absence of illumination. The photodetectors can hence be calibrated also for measuring temperature. Since during the thermal cycle the light sources 30, 31 are turned off, reading of the resistance of the photodetectors 104 indicates the temperature at the wells 108.

Figure 14:
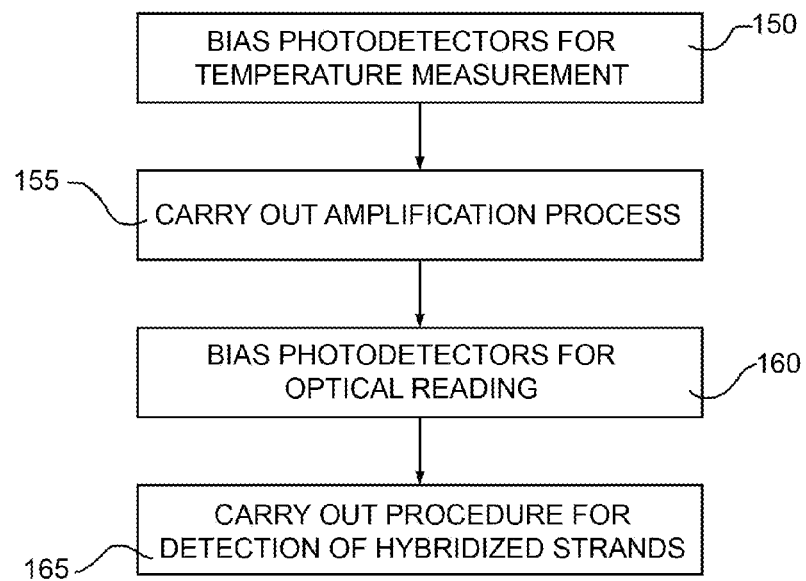
FIG. 14 is a flowchart regarding a method of carrying out a biochemical process according to a different embodiment.

With reference to FIG. 14, the control unit 25 initially biases the photodetectors 104 for the temperature measurement (block 150), then performs the amplification process (block 155), with the thermal cycles required. In this step, the control unit 25 uses the photodetectors 104 as temperature sensors.

Next (block 160), the control unit 25 biases the photodetectors 104 for the optical reading and executes the procedure for detection of hybridized strands already described with reference to FIG. 10 (block 165), during which the photodetectors 104 are used for calibration of the light sources 30, 31.

Use of the photodetectors 104 as temperature sensors enables saving in terms of components (the autonomous temperature sensor) and makes it possible to have available a number of temperature detections, made in the immediate vicinity of the wells 108. The measurements are hence precise and reliable. Furthermore, the absence of the temperature sensor on the back of the support 102 enables occupation of the entire area corresponding to the well module 103 so as to have a more uniform distribution of temperature when the heater 105 is activated.

Figure 15:
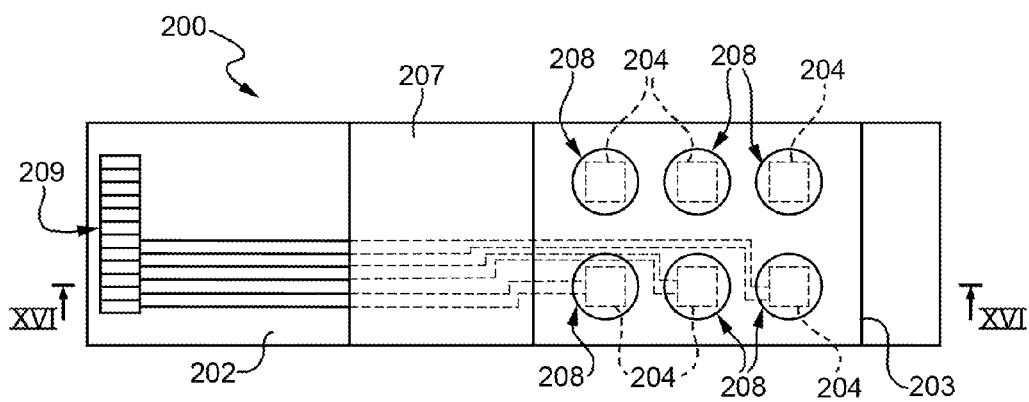
FIG. 15 is a top plan view of a cartridge for biochemical analyses according to a further embodiment.
Figure 16:
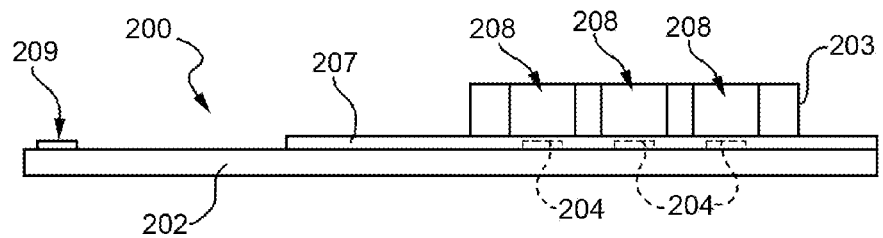
FIG. 16 is a side view of the cartridge of FIG. 15, sectioned in the plane of trace XVI-XVI of FIG. 15.

According to the embodiment illustrated in FIGS. 15 and 16, a calibration cartridge 201 comprises a support 202, in particular a PCB card, on which discrete photodetectors 204 are mounted. The photodetectors 204 are connected to terminals of a connector 209 through printed paths 201 and are embedded in an insulating layer 207, which coats a part of the support 202. Insulating layer 207 could be transparent to light radiation in substantially the entire visible spectrum.

A well module 203, comprising a plurality of wells 208 is glued on the insulating layer 207.

The calibration cartridge 200 has dimensions that render it suitable for being inserted into the slot 15 of the analyser 10. In addition, the photodetectors 204 and the wells 208 are arranged so as to occupy, when the calibration cartridge 200 is in the slot 15, positions corresponding to positions of wells of a microreactor loaded in the analyser 10, i.e., in the proximity of the windows 16, 17.

In this case, the calibration of the light sources 30, 31 is made using the calibration cartridge 200. Once calibration is through, the calibration cartridge 200 is replaced with a cartridge comprising a microreactor, and the steps of amplification and detection of the hybridized strands are executed using the calibration data determined previously.

The insulating layer 207 and the well module 203 enable faithful reproduction of the conditions of illumination that obtain when a microreactor is loaded into the analyser 10.

Modifications and variations may be made to the device and to the method described herein, without thereby departing from the scope of the present invention, as defined in the annexed claims.

What is claimed is:

1. A system for biochemical analyses comprising:
   an analyzer comprising a light source configured to illuminate a plurality of positions with light radiation, wherein the analyzer is configured to receive a plurality of wells such that each position is occupied by a respective well and is configured to receive a plurality of photodetectors such that each position is occupied by a respective photodetector, the analyzer further comprising an image sensor configured to acquire images of the plurality of wells occupying the plurality of positions and illuminated with the light radiation from the light source; and
   a control unit configured to use the photodetectors to determine for each position an incident optical power of the light radiation from the light source based on an output of a photodetector occupying that position, to obtain the images of the illuminated wells from the image sensor, and to compensate the images of the illuminated wells as a function of the incident optical power determined for the positions.

2. The system according to claim 1, wherein the plurality of wells and the plurality of photodetectors are located in a cartridge such that each well has a corresponding photodetector, and wherein the analyzer is configured to receive the cartridge such that each position is occupied by a respective well and a respective photodetector.

3. The system according to claim 2, wherein the control unit is configured to determine a temperature at the wells through the photodetectors.

4. The system according to claim 1, wherein the plurality of wells is located in a microreactor cartridge and the plurality of photodetectors is located in a calibration cartridge separate from the microreactor cartridge, and wherein the analyzer is configured to receive the microreactor cartridge such that each position is occupied by a respective well and is configured to receive the calibration cartridge such that each position is occupied by a respective photodetector.

5. The system according to claim 1, further comprising a memory module accessible by the control unit, wherein the memory module contains for each photodetector:
   a first response curve, calibrated and normalized as a function of wavelength;
   a second response curve, calibrated and normalized as a function of angle of incidence; and
   an incidence angle of the light radiation coming from the light source.

6. The system according to claim 5, wherein the control unit is configured to determine the incident optical power for each position using the respective first and second response curves for the photodetector occupying that position.

7. The system according to claim 1, wherein the control unit is housed in the analyzer.

8. A system for biochemical analyses comprising:
   a cartridge, wherein the cartridge comprises a plurality of wells and a plurality of photodetectors such that each well has a corresponding photodetector;
   an analyzer configured to receive the cartridge, wherein the analyzer comprises a light source configured to illuminate the plurality of wells with light radiation, wherein the analyzer further comprises an image sensor configured to acquire images of the plurality of wells illuminated by the light radiation from the light source; and
   a control unit configured to use the photodetectors to determine for each well an incident optical power of the light radiation from the light source based on an output of the photodetector corresponding to that well, to obtain the images of the illuminated wells from the image sensor, and to compensate the images of the illuminated wells as a function of the incident optical power determined for the wells.

9. The system according to claim 8, further comprising a memory module accessible by the control unit, wherein the memory module contains for each photodetector:
   a first response curve, calibrated and normalized as a function of wavelength;
   a second response curve, calibrated and normalized as a function of angle of incidence; and
   an incidence angle of the light radiation coming from the light source.

10. The system according to claim 9, wherein the control unit is configured to determine the incident optical power for each well using the respective first and second response curves for the photodetector corresponding to that well.

11. The system according to claim 8, wherein the control unit is housed in the analyzer.

12. A system for biochemical analyses comprising:
   an analyzer comprising a light source configured to illuminate a plurality of positions with light radiation, wherein the analyzer is configured to receive a plurality of wells such that each position is occupied by a respective well and is configured to receive a plurality of photodetectors such that each position is occupied by a respective photodetector, the analyzer further comprising an image sensor configured to acquire images of the plurality of wells occupying the plurality of positions and illuminated with the light radiation from the light source;
   a control unit configured to use the photodetectors to determine for each position an incident optical power of the light radiation from the light source based on an output of a photodetector occupying that position, to obtain the images of the illuminated wells from the image sensor, and to compensate the images of the illuminated wells as a function of the incident optical power determined for the positions; and a memory module accessible by the control unit, wherein the memory module contains for each photodetector:
a first response curve, calibrated and normalized as a function of wavelength;
a second response curve, calibrated and normalized as a function of angle of incidence;
an incidence angle of the light radiation coming from the light source; and
an incident optical power of the light radiation from the light source determined by the control unit.

13. The system according to claim 12, wherein the plurality of wells and the plurality of photodetectors are located in a cartridge such that each well has a corresponding photodetector, and wherein the analyzer is configured to receive the cartridge such that each position is occupied by a respective well and a respective photodetector.

14. The system according to claim 12, wherein the plurality of wells is located in a microreactor cartridge and the plurality of photodetectors is located in a calibration cartridge separate from the microreactor cartridge, and wherein the analyzer is configured to receive the microreactor cartridge such that each position is occupied by a respective well and is configured to receive the calibration cartridge such that each position is occupied by a respective photodetector.

* * * * *

UNITED STATES PATENT AND TRADEMARK OFFICE
CERTIFICATE OF CORRECTION

PATENT NO. : 8,753,869 B2
APPLICATION NO. : 13/531303
DATED : June 17, 2014
INVENTOR(S) : Maria Eloisa Castagna et al.

It is certified that error appears in the above-identified patent and that said Letters Patent is hereby corrected as shown below:

On the Title page, item [75] of Inventors, change "Alberto Mario Piro" to "Alberto Maria Piro"

Signed and Sealed this
Eighteenth Day of August, 2015

Michelle K. Lee
*Director of the United States Patent and Trademark Office*